United States Patent [19]
Snow et al.

[11] Patent Number: 6,007,546
[45] Date of Patent: Dec. 28, 1999

[54] INJECTION SNARE

[75] Inventors: Todd H. Snow, Westborough, Mass.; Vincent J. Testa, Grand Rapids, Mich.

[73] Assignees: Boston Scientific Ltd., St. Michael, Barbados; SCIMED Life Systems, Inc., Maple Grove, Minn.

[21] Appl. No.: 09/178,569

[22] Filed: Oct. 26, 1998

[51] Int. Cl.[6] ................................................. A61B 17/24
[52] U.S. Cl. ........................... 606/113; 606/114; 606/110
[58] Field of Search .............................. 606/1, 110, 113, 606/114, 127, 167, 184, 185; 604/164, 187, 264, 272

[56] References Cited

U.S. PATENT DOCUMENTS

| | | |
|---|---|---|
| 1,606,497 | 11/1926 | Berger . |
| 4,222,380 | 9/1980 | Terayama . |
| 5,026,371 | 6/1991 | Rydell et al. . |
| 5,066,295 | 11/1991 | Kozak et al. . |
| 5,084,054 | 1/1992 | Bencini et al. . |
| 5,158,561 | 10/1992 | Rydell et al. . |
| 5,171,314 | 12/1992 | Dulebohn . |
| 5,190,542 | 3/1993 | Nakao et al. . |
| 5,190,555 | 3/1993 | Wetter et al. . |
| 5,201,740 | 4/1993 | Nakao et al. . |
| 5,201,741 | 4/1993 | Dulebohn . |
| 5,207,686 | 5/1993 | Dolgin . |
| 5,336,227 | 8/1994 | Nakao et al. . |
| 5,376,094 | 12/1994 | Kline . |
| 5,417,697 | 5/1995 | Wilk et al. . |
| 5,423,830 | 6/1995 | Schneebaum et al. . |
| 5,462,553 | 10/1995 | Dolgin . |
| 5,480,404 | 1/1996 | Kammerer et al. . |
| 5,486,182 | 1/1996 | Nakao et al. . |
| 5,542,948 | 8/1996 | Weaver et al. . |
| 5,746,747 | 5/1998 | McKeating ........................ 606/113 |
| 5,752,961 | 5/1998 | Hill ................................. 606/113 |
| 5,846,248 | 12/1998 | Chu et al. ......................... 606/113 |
| 5,891,153 | 4/1999 | Peterson ........................... 606/113 |

*Primary Examiner*—Glenn K. Dawson
*Attorney, Agent, or Firm*—Kenyon & Kenyon

[57] ABSTRACT

An injection snare is disclosed. One embodiment of the present invention includes an instrument body, an actuator slidably attached to the body, a catheter attached to and extending through the body at a proximal end of the catheter, an injection needle, and a snare. The injection needle is disposed within the catheter and has a proximal end connected to the actuator. A distal end of the injection needle contains a piercing tip. The injection needle is movable within the catheter between a first position wherein the distal end of the needle extends beyond the distal end of the catheter and a second position wherein the distal end of the needle is retracted within said catheter. The snare is attached to the distal end of the injection needle.

25 Claims, 10 Drawing Sheets

INJECTION SNARE

BACKGROUND OF THE INVENTION

The present invention relates to a surgical instrument for removing tissue from a patient. More specifically, the invention provides a capability to both inject fluid into the tissue that is to be removed and to remove the tissue by utilizing a single instrument. Pending U.S. patent application Ser. No. 08/421,409 filed Apr. 13, 1995 is a related application to this application.

During endoscopic tissue removal procedures, often referred to as polypectomy or endoscopic mucosal resection, it is often necessary to inject fluid submucosally into the tissue to be removed to raise the lesion off of the muscularis propria to prevent thermal injury of the muscle layer during excision by cautery. Large pedunculated polyps may also require an injection of fluid into the stalk, prior to cauterization, to prevent hemorrhage. Additionally, tissue that is suspected to be cancerous at the site of interest may be "tattooed" or injected using India ink. This is a permanent marker that allows for surveillance during subsequent procedures. Therefore, there are many situations where an injection needle is required in order to inject fluid into tissue that is to be removed.

Currently, in a procedure where fluid is injected into tissue and the tissue is subsequently removed from the body, separate instruments are utilized to inject the fluid and to cut and remove the tissue. The requirement to use two separate instruments to perform these tasks presents drawbacks. One of these drawbacks is the time required to perform the procedure. By requiring the surgeon to utilize two separate instruments, the time required to perform the complete procedure is increased. Additionally, when using separate instruments, the fluid which is injected into the tissue often dissipates during the time it takes to remove the injection needle from the body and insert a snare through the working channel of an endoscope and into the body. Thus, the utility of the fluid injection step may be diminished greatly. Therefore, it would be desirable to provide a single instrument that could both inject fluid into the tissue to be removed and separate the tissue from the body. The use of a single device would improve the efficiency of conducting these procedures.

An additional drawback with current tissue removal devices and procedures is associated with the removal of the tissue after it has been separated from the body. Currently, retrieval devices such as baskets and webs are inserted through a lumen in an endoscope and are positioned within the body to capture the removed tissue. However, these devices require the surgeon to manipulate an additional apparatus and can be difficult to position within the body. Therefore, it would be desirable to provide an improved method and apparatus for capturing tissue after it has been separated from the body.

SUMMARY OF THE INVENTION

The present invention is directed to an injection snare. One embodiment of the present invention includes an instrument body, an actuator slidably attached to the body, a catheter attached to and extending through the body at a proximal end of the catheter, an injection needle, and a snare. The injection needle is disposed within the catheter and has a proximal end connected to the actuator. A distal end of the injection needle contains a piercing tip. The injection needle is movable within the catheter between a first position wherein the distal end of the needle extends beyond the distal end of the catheter and a second position wherein the distal end of the needle is retracted within said catheter. The snare is attached to the distal end of the injection needle.

DETAILED DESCRIPTION

Figure 1:
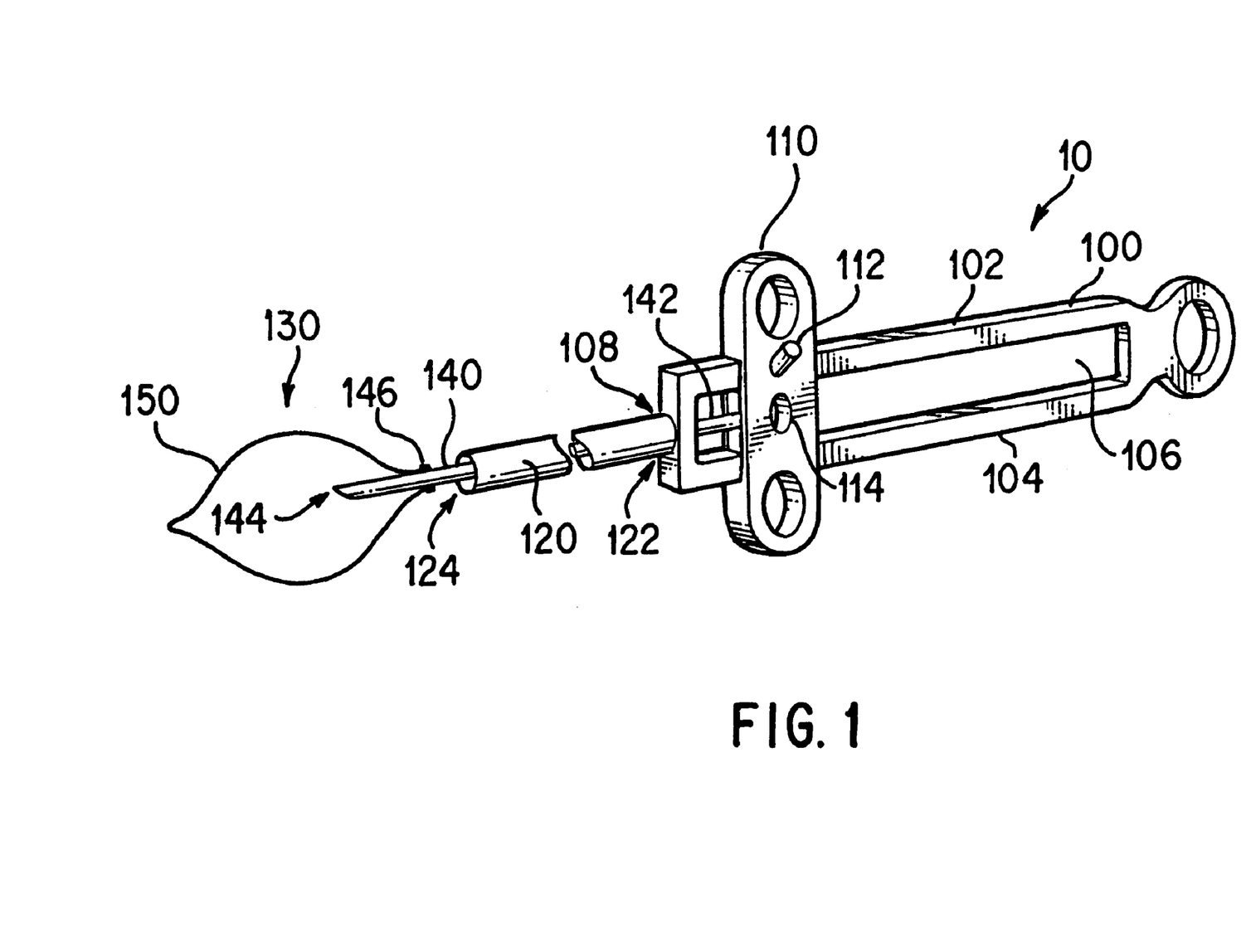
FIG. 1 is a perspective view of one embodiment of the present invention with the injection snare extended from the catheter.

FIG. 1 illustrates a first embodiment for the injection snare 130 of the present invention. As can be seen, injection snare 130 is contained within surgical instrument assembly 10. Surgical instrument assembly 10 includes body 100, actuator 110, and catheter 120. Body 100 is comprised of a first rail 102 and a second rail 104. First rail 102 and second rail 104 are opposed to each other and define a channel 106 therebetween. Actuator 110 is attached to body 100 and is configured for slidable motion along rails 102 and 104 of body 100. Catheter 120 is a flexible tube structure and is attached at a proximal end 122 thereof to body 100. Catheter 120 extends from body 100 in a distal direction and contains an opening at the distal end 124 of the catheter. The proximal end 122 of catheter 120 is attached to body 100 and extends through aperture 108 that is included in body 100.

Injection snare 130 is comprised of two components, namely, injection needle 140 and snare 150. Injection needle 140 is comprised of an electrically conductive material and extends through catheter 120 and through aperture 108 in body 100. The proximal end 142 of injection needle 140 is attached to actuator 110. Actuator 110 includes conductor 112 and injection port 114. As will be further explained later in this specification, conductor 112 is utilized to conduct an electrical current through injection needle 140 and into snare 150. Injection port 114 is utilized to provide fluid to injection needle 140 such that the fluid can be injected into the body of a patient by the injection needle.

In further describing injection needle 140 and snare 150, the needle contains a distal end 144. Distal end 144 defines a tissue piercing tip. The piercing tip that is included at distal end 144 of injection needle 140 is utilized to pierce a lesion that is in the body of a patient such that fluid can be provided to the lesion through injection needle 140. Attached to needle 140 at its distal end 144 is snare 150. Snare 150 is a cauterization loop that is utilized to capture a polyp within the snare and cut the polyp from the body. Thus, snare 150 is also comprised of an electrically conductive material. Snare 150 may be formed in either a generally circular shape or in a generally oval configuration, with the only requirement being that its shape permit capturing a polyp within the snare.

As is illustrated in FIG. 1, snare 150 is attached to injection needle 140 at connection joint 146. Connection joint 146 provides for a conductive path between needle 140 and snare 150 so that, when an electrical current is provided to injection needle 140 through conductor 112, the electrical current will be conducted along injection needle 140 from its proximal end to its distal end and will pass through connection joint 146 and into snare 150. As such, snare 150 can be energized to cut a polyp from the body that is captured within snare 150 and can be used to cauterize the severed membrane.

As stated previously, snare 150 is directly attached to injection needle 140 at connection joint 146 such that an electrical current may be conducted through injection needle 140 and into snare 150. Therefore, connection joint 146 may be comprised of any of a variety of different materials, with the only requirement being that an electrical current must be able to be conducted through the joint. The joining of snare 150 and injection needle 140 may be achieved by utilizing, for example, an electrically conductive adhesive, a weld between the snare and the injection needle, or by soldering the snare to the needle. The present invention is not limited to any particular methodology for joining snare 150 to injection needle 140. The only requirement is that the joint provide adequate strength and electrical conductivity between the snare and the injection needle.

When joining snare 150 to injection needle 140, the joint between snare 150 and needle 140 can be along any length of injection needle 140. Additionally, the actual point of attachment between snare 150 and injection needle 140 at distal end 144 of the injection needle can be at any point. The only requirement is that when the injection needle 140 is extended from catheter 120, the snare 150 is also deployed from catheter 120 and when the needle 140 is retracted within the catheter 120 the snare 150 can also be fully retracted within the catheter.

Figure 2:
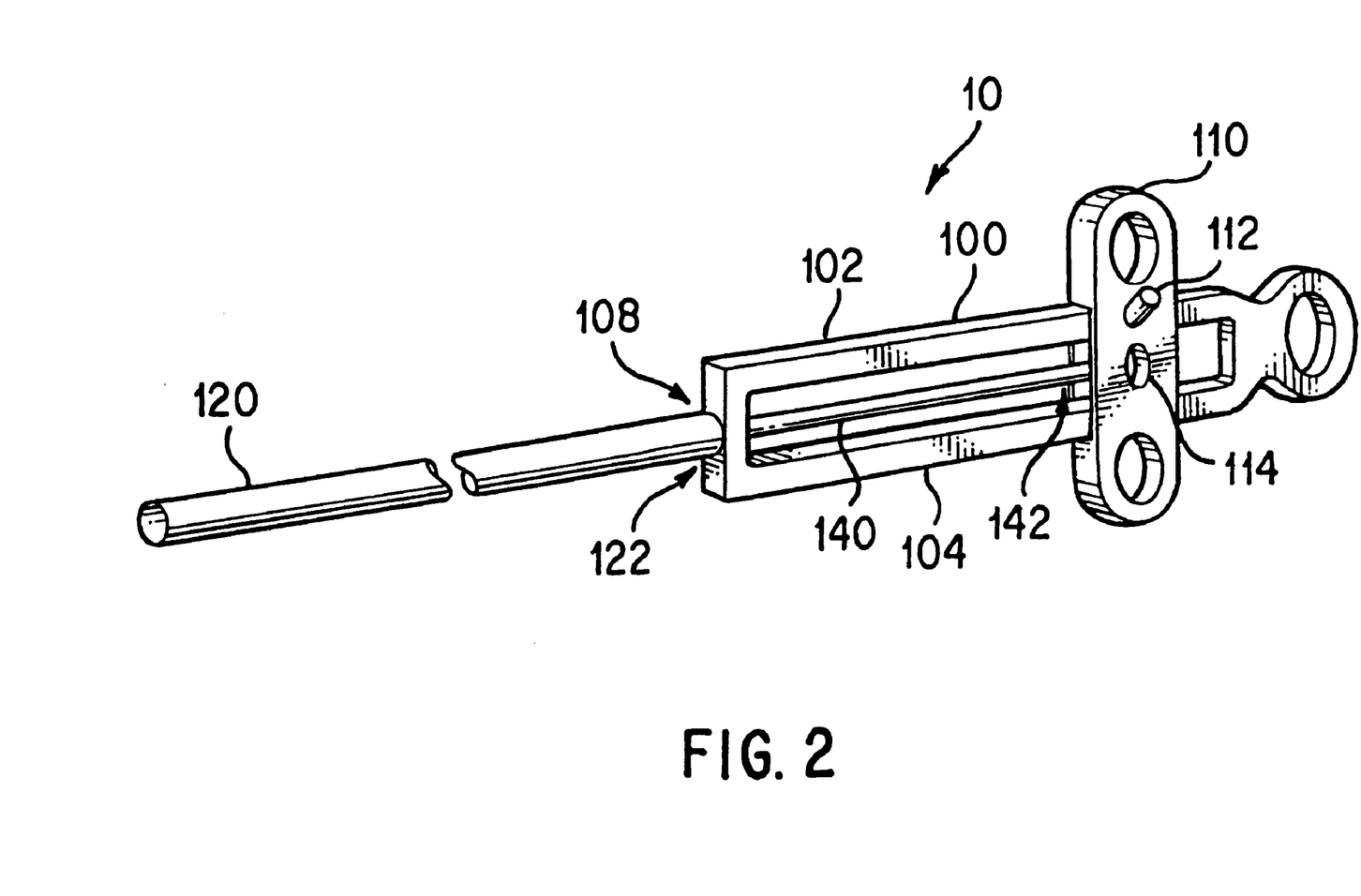
FIG. 2 illustrates the present invention as embodied in FIG. 1 where the injection snare has been retracted into the catheter by sliding the actuator towards the proximal end of the instrument body.

FIG. 1 illustrates injection snare 130 in a first position where the distal end 144 of injection needle 140 and snare 150 extend beyond the distal end 124 of catheter 120. In this first position, injection snare 130 may be utilized to inject a polyp with fluid by utilizing injection needle 140 and to grasp and cut the polyp from the body by utilizing snare 150. FIG. 2 illustrates injection snare 130 where the injection snare has been moved to a second position such that the injection snare has been fully retracted within the catheter 120. Movement of injection snare 130 within catheter 120 is achieved by sliding actuator 110 along body 100 in a proximal direction. Since injection needle 140 is attached to actuator 110 at the proximal end 142 of injection needle 140, movement of actuator 110 in an proximal direction will also move needle 140 in the proximal direction, thus retracting distal end 144 of injection needle 140 into catheter 120. Since snare 150 is attached to distal end 144 of injection needle 140, retraction of injection needle 140 within catheter 120 will also retract snare 150 within catheter 120.

Figure 3:
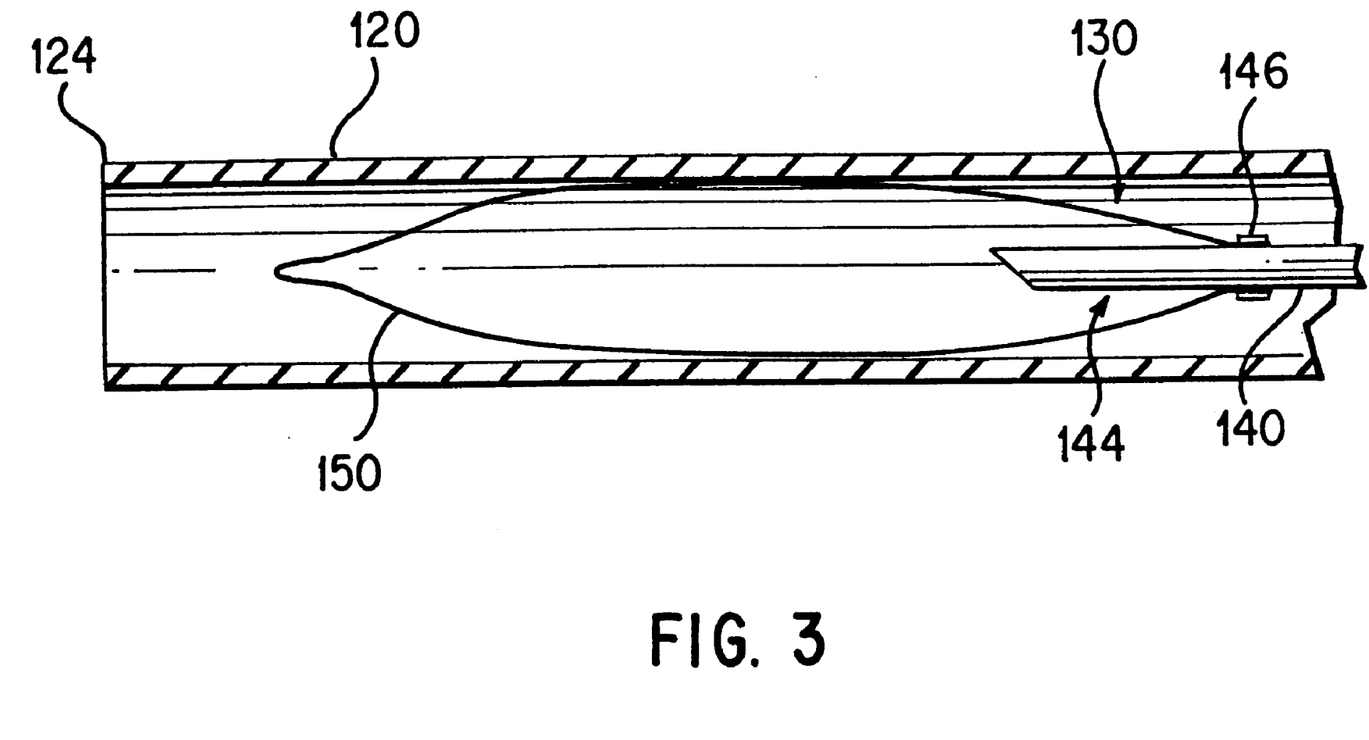
FIG. 3 is a cross-section view of the catheter with the injection snare retracted into the catheter.

FIG. 3 is a cross sectional view of injection snare 130 when it is in its second position retracted within catheter 120. As can be seen, snare 150 is entirely retracted within catheter 120. Since snare 150 extends beyond distal end 144 of injection needle 140, actuator 110 must be able to be moved a sufficient distance in a proximal direction along body 100 such that needle 140 is retracted within catheter 120 a distance such that snare 150 is able to be fully retracted within catheter 120. As can be seen, when snare 150 is fully retracted within catheter 120, snare 150 collapses to a sufficient degree such that the loop formed by snare 150 is able to be compressed and retracted within catheter 120.

Figure 4:
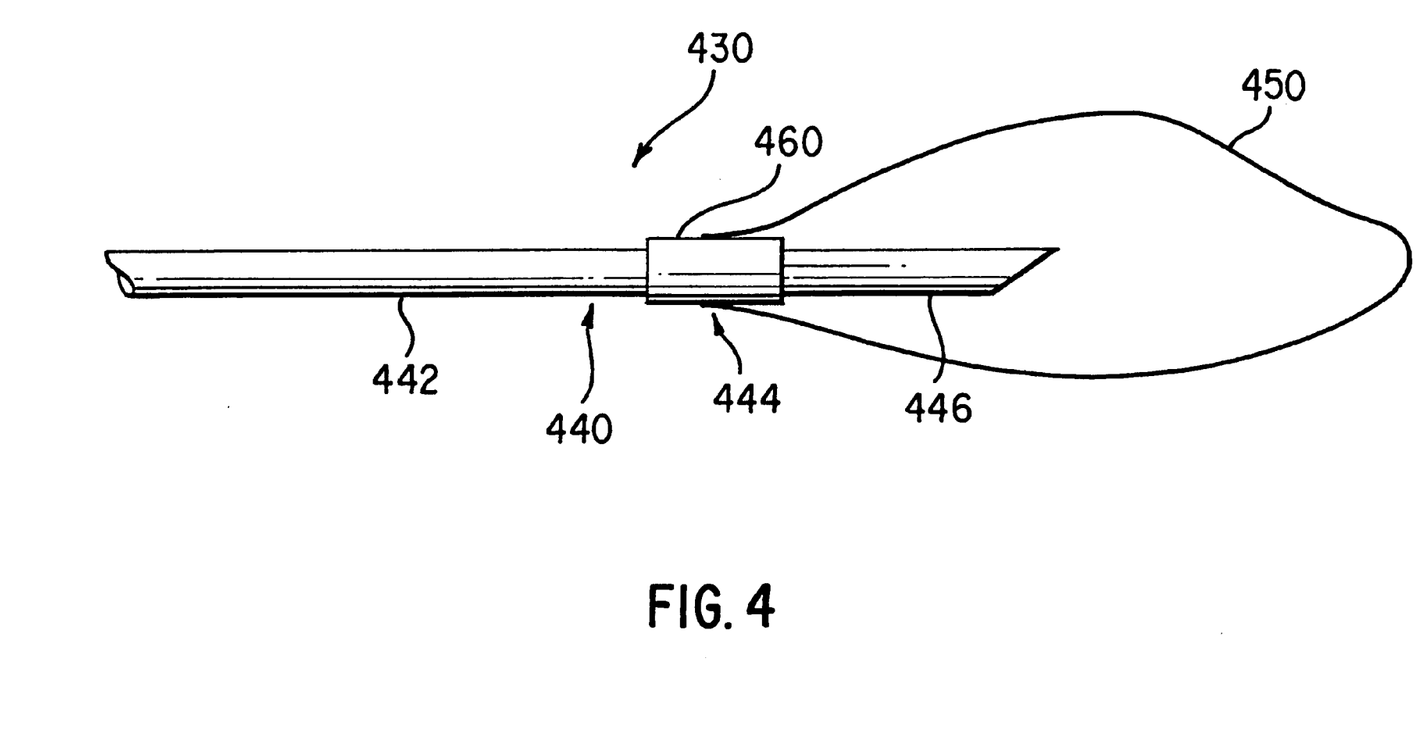
FIG. 4 illustrates a second embodiment for the injection snare of the present invention.

FIG. 4 illustrates a second embodiment for the injection snare 430 of the present invention. As can be seen in FIG. 4, injection snare 430 includes injection needle 440 and snare 450. The function of the embodiment for the injection snare 430 as disclosed in FIG. 4 is the same as that described for the embodiment of FIGS. 1–3, i.e., to provide for both fluid injection and polyp capturing and cutting in a single device. However, the structural difference in the embodiment of FIG. 4 as opposed to the embodiment of FIGS. 1–3 is that in the embodiment of FIG. 4, injection needle 440 is comprised of a first electrically conducting portion 442 and a second non-electrically conducting portion 446. First portion 442 and second portion 446 are joined by electrically conducting coupler 460. As can be seen, snare 450 is attached to injection needle 440 by attaching snare 450 to coupler 460.

The purpose of comprising injection needle 440 out of a first electrically conducting portion 442 and a second non-electrically conducting portion 446 is that by using an electrically non-conductive material for second portion 446, the second portion can be manufactured from a somewhat more flexible material, such as plastic, than that utilized for electrically conductive portion 442. It may be desirable to utilize a more flexible material for second portion 446 so that the needle would still be able to penetrate the polyp to provide fluid to the polyp but yet not be so rigid such that it could possibly pierce the catheter as it is retracted and extended from the catheter.

There can be a variety of configurations for coupler 460 and the present invention is not limited to any particular configuration. The only requirement is that coupler 460 must be comprised of an electrically conductive material and must join first portion 442 to second portion 446 and be capable of providing electrical connectivity to snare 450. As such, coupler 460 can join first needle portion 442 to second needle portion 446 by friction fitting the first portion and the second portion within the coupler or can utilize an adhesive to join the first portion and the second portion to the coupler. However, if an adhesive is utilized, the adhesive must be electrically conductive, at least where the adhesive is utilized to join first electrically conductive portion 442 to coupler 460.

As described previously for the embodiment of FIGS. 1–3, snare 450 can be attached to coupler 460 by using any of a variety of means, including welding, an electrically conductive adhesive, or soldering. Again, all that is required is that the attachment point between snare 450 and coupler 460 be electrically conductive and that it be of sufficient strength such that snare 450 will remain attached to injection needle 440 during repeated retractions and extensions from the catheter.

Whereas second portion 446 has been described as being comprised of an electrically non-conductive material, it is not necessary that the material be electrically non-conductive. What is desirable is that the second portion be comprised of a somewhat flexible material. It was suggested that the second portion could be comprised of a non-electrically conductive material because these materials are likely to be more flexible than electrically conductive materials. However, any material that has a structure such that it is not likely to pierce the catheter but yet is rigid enough to penetrate a polyp, whether electrically conductive or non-conductive, can be utilized for second portion 446.

Figure 5:
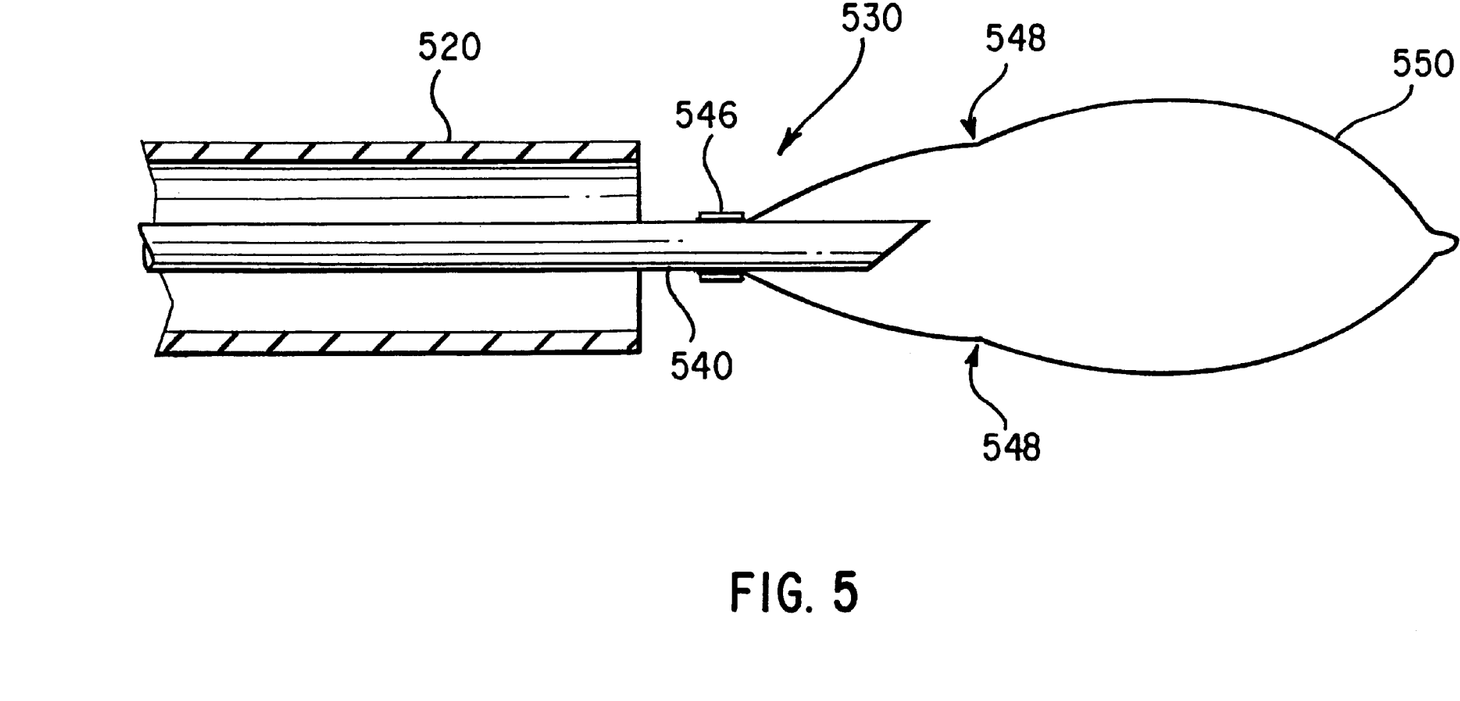
FIG. 5 is a cross-section view of a third embodiment for the injection snare of the present invention with the injection snare extended from a catheter.

FIG. 5 is a cross sectional view of a third embodiment for the injection snare 530 of the present invention. FIG. 5 illustrates the injection snare in its extended first position from catheter 520. As is illustrated in FIG. 5, snare 550 is again attached to injection needle 540 at connection joint 546 as was previously described in this specification. However, in the embodiment of FIG. 5 for the injection snare, snare 550 includes a bend 548 in a location along the snare that is proximate to the attachment point between the injection needle and the snare. The bend 548 in snare 550 is included on both sides of snare loop 550 and each bend is similar in configuration. The specific location of bends 548 in snare loop 550 and the exact degree of the bend in the snare loop are not rigidly defined. The purpose of the bends in the snare wire is to allow snare 550 to be fully operable, i.e., expanded, even when needle 540 has been retracted into catheter 520. This configuration for snare 550, where it is still maintained in a fully expanded position even though injection needle 540 has been retracted into catheter 520, can be seen in FIG. 6.

Figure 6:
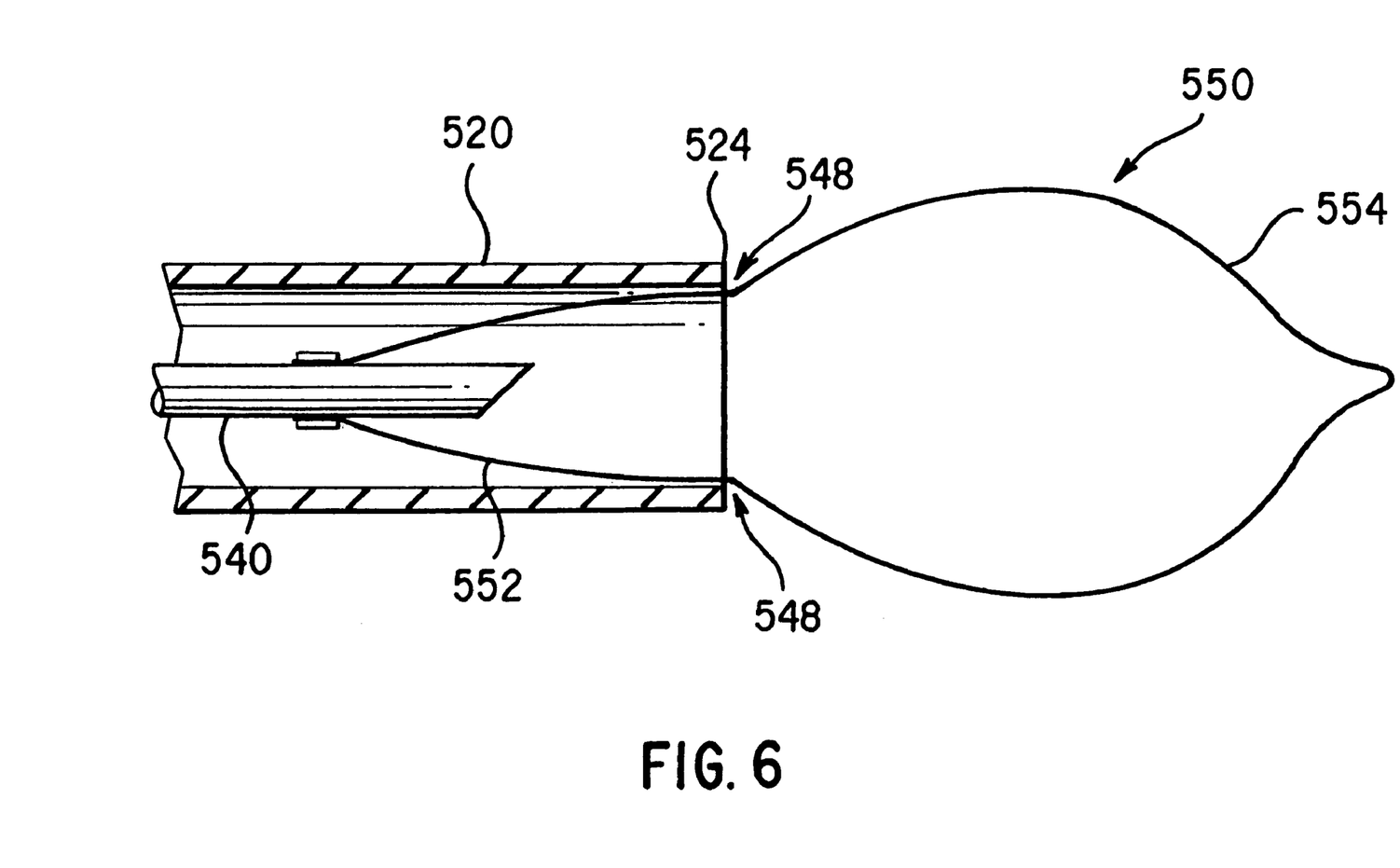
FIG. 6 is a cross-section view of the embodiment of FIG. 5 for the injection snare with the injection snare partially retracted within the catheter.

As illustrated in FIG. 6, injection needle 540 has been retracted fully into catheter 520. When injection needle 540 has been retracted to this position, bends 548 in snare 550 are positioned at the distal end 524 of catheter 520. Thus, in this position, a first portion 552 of snare loop 550 is retracted within catheter 520 and a second portion 554 of snare loop 550 is still fully expanded outside of catheter 520. If bends 548 in snare loop 550 were not provided, when injection needle 540 was retracted within catheter 520 to a position as illustrated in FIG. 6, snare loop 550 would be compressed to such an extent that it would not be able to function to snare a polyp.

It may be desirable to provide for bends 548 in snare loop 550 to allow the physician to have better control of the needle's positioning when performing a procedure, i.e., the ability to control the needle's extension such that it is able to be extended to pierce a polyp and be retracted into the catheter so that it is out of the way of the snare when the physician is utilizing the snare. Without this configuration for snare 550, it could be possible that needle 540 would have to remain deployed from the catheter even after it has preformed its function, thus possibly hindering the physician's use of the snare.

Figure 7:
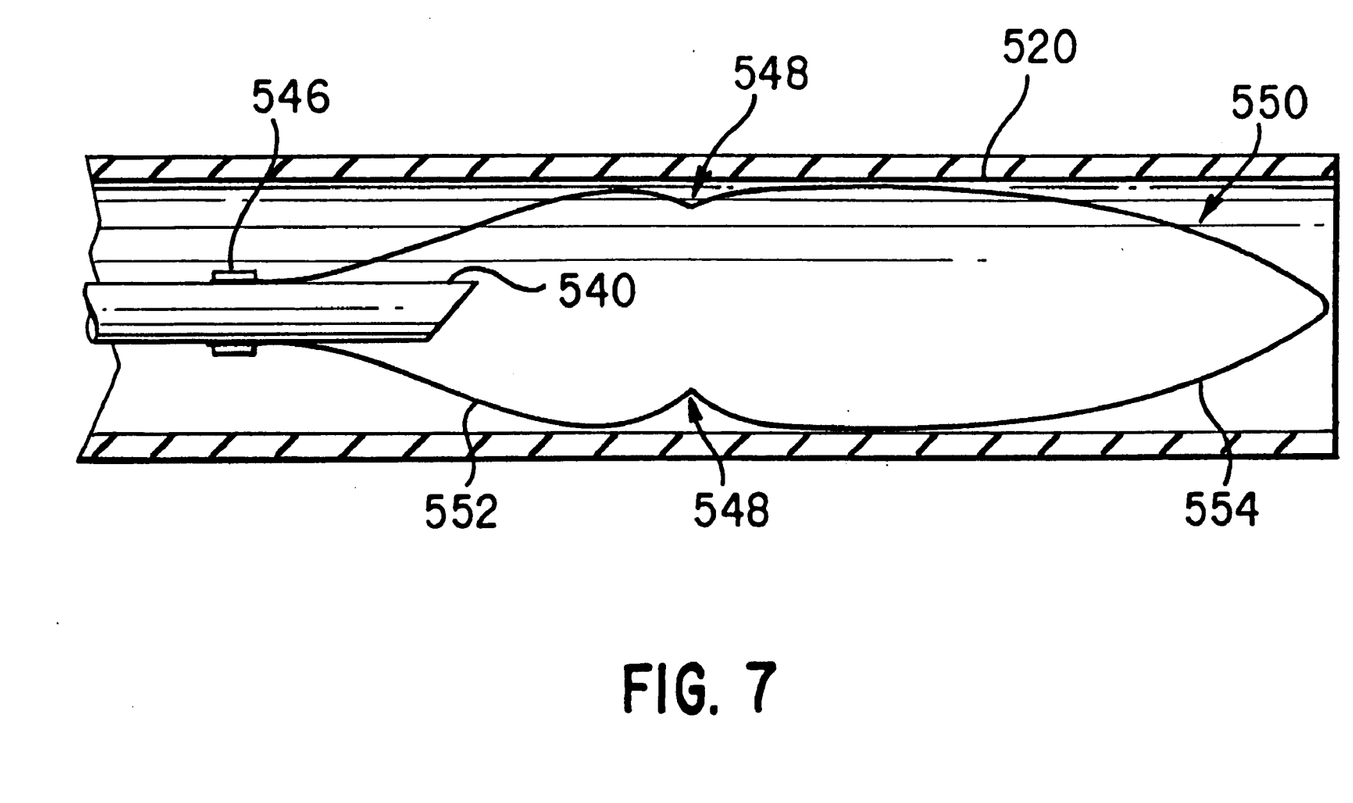
FIG. 7 is a cross-section view of the embodiment of FIG. 5 for the injection snare with the injection snare fully retracted within the catheter.

FIG. 7 is a cross-sectional view of the embodiment of FIG. 5 for snare loop 550 showing injection needle 540 and snare loop 550 when needle 540 has been retracted further into catheter 520. When injection needle 540 has been retracted into catheter 520 to the position as illustrated in FIG. 7, snare loop 550 has now been fully retracted into catheter 520.

Figure 8:
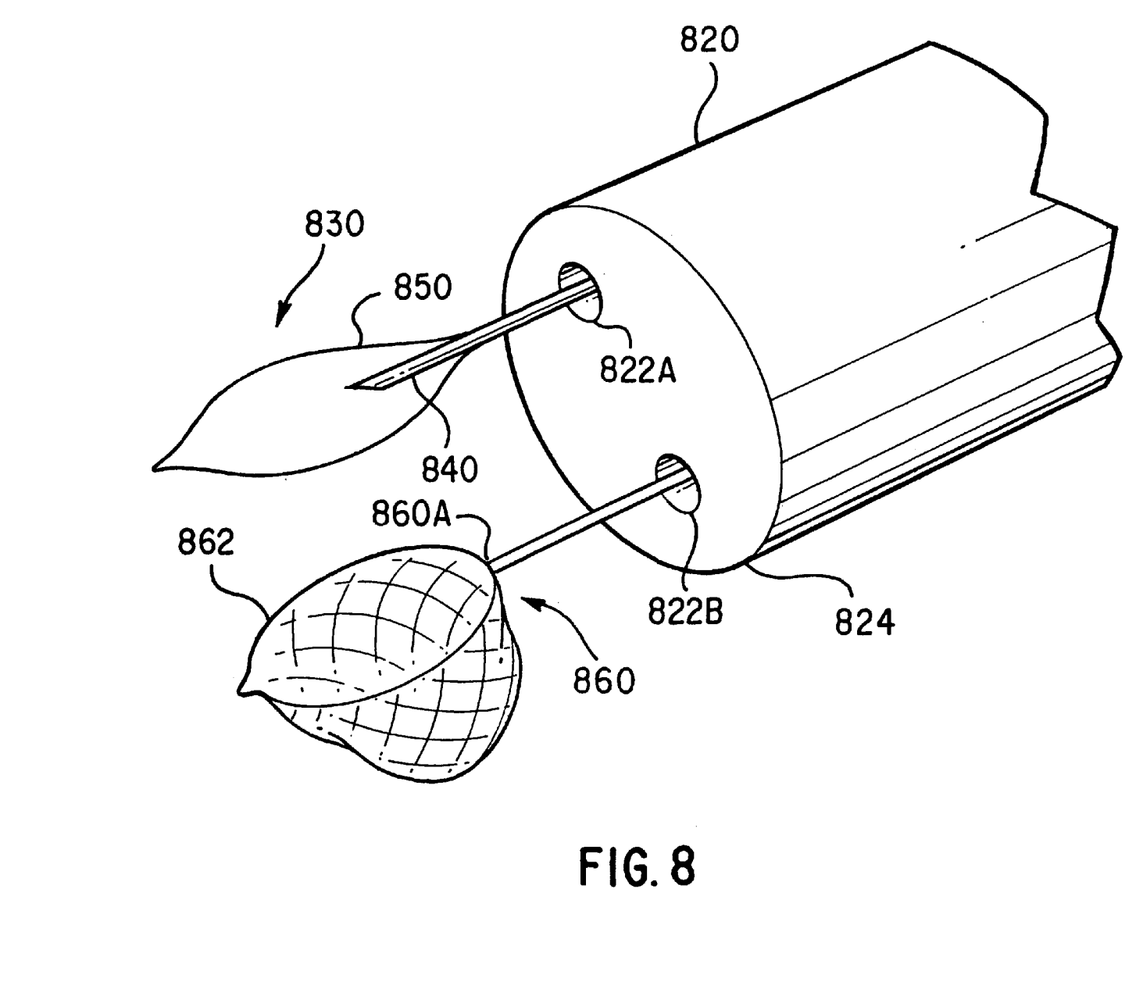
FIG. 8 is a perspective view of an injection snare as used in combination with a retrieval device that is contained in a second lumen of a surgical instrument assembly.

FIG. 8 is a perspective view of an embodiment of the injection snare of the present invention as used in combination with a retrieval device that is contained in a second lumen in a surgical instrument assembly. As can be seen in FIG. 8, catheter 820 includes a first lumen 822A and a second lumen 822B. Disposed within first lumen 822A is injection snare 830. As previously disclosed, injection snare 830 is comprised of an injection needle 840 and a snare loop 850. For the instrument assembly of FIG. 8, the specific embodiment for injection needle 840 and snare loop 850 can be any of the embodiments previously disclosed, i.e., a single structural element for the injection needle, a dual-portion injection needle construction, or a bent snare loop configuration. Thus, injection snare 830 functions as previously described in this specification for injecting a polyp with a fluid by utilizing injection needle 840 and for snaring and cutting the polyp by utilizing snare 850. The embodiment of FIG. 8, however, utilizes a second lumen 822B within catheter 820 to deploy a second instrument for use in combination with the injection snare 830. As illustrated in FIG. 8, the second instrument that is disposed within the second lumen 822B is a retrieval device 860 that includes a basket 862 disposed on a distal end 860A of the instrument. Retrieval device 860 would be utilized to capture and retrieve a polyp from the body that has been injected with fluid by utilizing injection needle 840 and cut and cauterized by using snare loop 850. After the polyp has been injected and severed from the body, the polyp would be captured within basket 862 of retrieval device 860 and removed from the body.

Whereas retrieval device 860 has been disclosed as being a basket, the retrieval device can be comprised of any known retrieval device, e.g., a net or forceps. In fact, it is not even required that a retrieval device be disposed within second lumen 822B. Any second instrument that could be useful to a surgeon when used in combination with the injection snare 830 of the present invention can be utilized in catheter 820. If retrieval device 860 was utilized within second lumen 822B of catheter 820, the second instrument could be extended and retracted from catheter 820 by utilizing an apparatus as was described for retracting and extending the injection snare, i.e., an actuator that is attached to the proximal end of the retrieval device. A second actuator device could be provided on the body of the surgical instrument and the second actuator device could operate independently of the first actuator device such that the injection snare could be operated independently of the second instrument that is disposed within the second lumen of the catheter.

Figure 9:
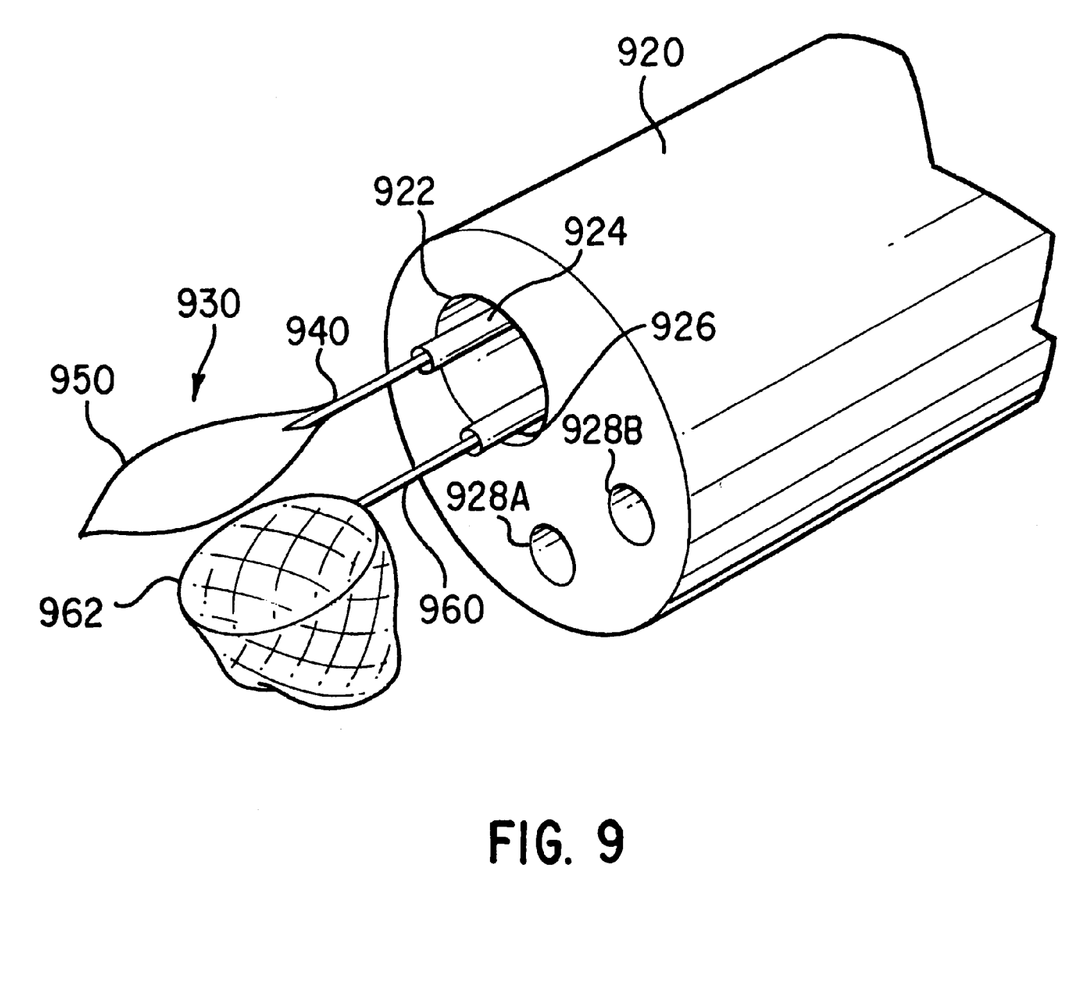
FIG. 9 is a perspective view of an injection snare as used with an endoscope assembly.

FIG. 9 illustrates an embodiment of the injection snare of the present invention as used in an endoscope assembly. As can be seen, endoscope assembly 920 includes a working channel 922 and a pair of apertures 928A and 928B for delivering light to, and receiving light from, a surgical site, respectively. Working channel 922 includes a first lumen 924 and a second lumen 926. Disposed within first lumen 924 is an injection snare 930 in accordance with the present invention. Injection snare 930 can be comprised of any of the embodiments discussed previously for the injection needle 940 and snare loop 950. Injection snare 930 would operate as previously described for injecting fluid into a polyp and for cutting and cauterizing the polyp by using snare 950. An actuator (not shown in FIG. 9) would be included at the proximal end of endoscope assembly 920 for extending injection snare 930 from lumen 924 and for retracting injection snare 930 within lumen 924. Disposed within second lumen 926 is retrieval device 960 which includes basket 962 at a distal end thereof Retrieval device 960 would operate as previously described in that it is used in combination with the injection snare to capture and remove a polyp from the patient's body after it has been injected with fluid and cut from the body. As such, retrieval device 960 can be extended from, and retracted into, second lumen 926. Retrieval device 960 would be extended and retracted from second lumen 926 by utilizing an actuator (not shown in FIG. 9) that would also be included at the proximal end of endoscope assembly 920. The injection snare 930 and retrieval device 960 could be independently operated and thus could be used in combination with each other in order to perform the surgical procedure.

Figure 10:
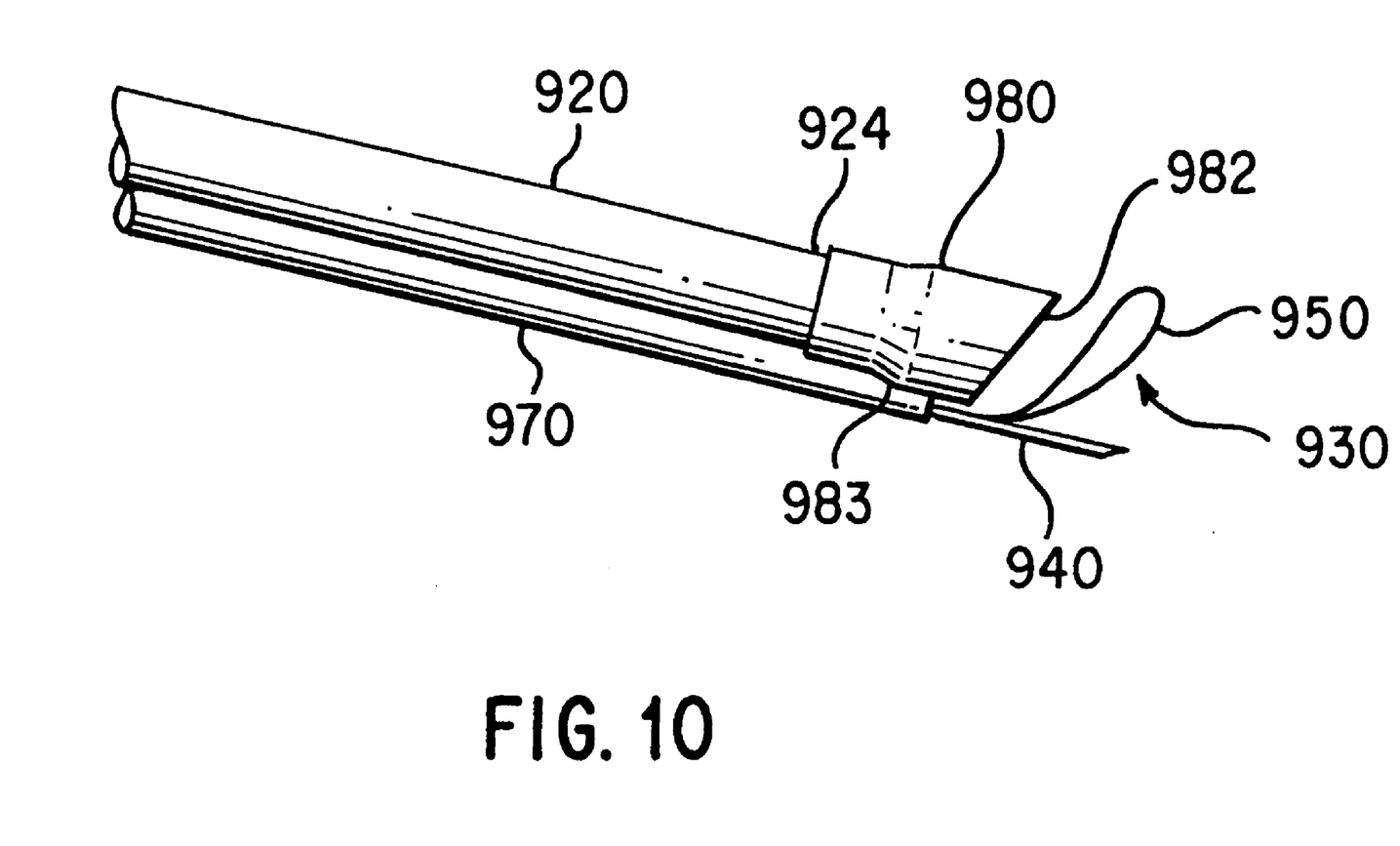
FIG. 10 illustrates an injection snare used in conjunction with a hooded endoscope assembly.

FIG. 10 illustrates a second embodiment for utilizing the injection snare 930 of the present invention with endoscope assembly 920. As opposed to the embodiment of FIG. 9, the embodiment of FIG. 10 utilizes a second working channel 970 within which is disposed injection snare 930. Second working channel 970 extends along the outside of endoscope assembly 920 and is attached to endoscope assembly 920. Second working channel 970 may be attached to endoscope assembly 920 by utilizing any attachment means, such as teflon tape. Injection snare 930 operates as previously described in order to inject a polyp with fluid through injection needle 940 and cut and cauterize the polyp by utilizing snare loop 950. However, in the embodiment of FIG. 10, a hood 980 is placed on the distal end 924 of the endoscope assembly. Hood 980 is an optically clear hood that allows the physician to visualize the polyp to be removed through the hood. Hood 980 may be attached to the distal end of endoscope assembly 920 by any of a variety of means, such as by friction fitting hood 980 onto the distal end of the endoscope assembly or by utilizing an adhesive to secure the hood to the endoscope assembly. Hood 980 is configured such that the top 982 of the hood is positioned at an angle with respect to the lower end 983 of the hood. The top of the hood can be provided with any desired angle so as to assist in advantageously positioning the hood with respect to the polyp.

In utilizing the endoscope assembly of FIG. 10, suction is provided through the first working channel of the endoscope assembly (not shown in FIG. 10). The suction is applied through the working channel in order to draw a polyp that is to be removed from the body into the hood 980 such that the polyp can be lifted up off of the surface of the membrane from which it is to be removed. This is desirable particularly with polyps that do not extend significantly up from the surface of the membrane to which they are attached and thus may be difficult to sever from the membrane.

As can also be seen in FIG. 10, snare 950 is bent such that it extends at a nearly right angle from the longitudinal axis of injection needle 940. As such, snare 950 lays substantially co-planar with, or parallel to, top 982 of hood 980. This is desirable so that the snare 950 may be advantageously positioned around the polyp so that the polyp may be severed at its base after it has been drawn into the hood.

Thus, in the embodiment of FIG. 10, injection snare 930 is not deployed through the working channel of the endoscope assembly 920, but rather, is deployed through an external, second channel 970 that is attached to the endoscope assembly 920. A suction is provided through the first working channel of the endoscope assembly in order to draw the polyp into hood 980 so that it may be severed by snare 950.

In operation, a user of an embodiment of the injection snare of the present invention would insert a distal end of a catheter into the body of a patient. By operating an actuator that is associated with the catheter, the user would extend an injection needle and a snare through the distal end of the catheter and into the body of the patient. Both the snare loop and the injection needle are inserted into the body as a single instrument and are positioned in proximity to the polyp that is to be removed. The operator then inserts the injection needle into the polyp and injects fluid into the polyp in order to raise the polyp from the membrane of the patient's body. After injecting fluid into the polyp, the operator captures the polyp with the snare loop and cuts and cauterizes the polyp by conducting an electrical current through the needle and into the snare loop. After the polyp has been cut from the body, the operator could capture the polyp in a retrieval device. The polyp is then removed from the body by removing the catheter from body.

Several variations on the disclosed embodiments are contemplated. For example, the injection snare of the present invention has been disclosed as being utilized in conjunction with an endoscope assembly and in conjunction with another embodiment of a surgical instrument that includes a body and an actuator. However, the present invention is not limited to any particular embodiment for the surgical tool with which the injection snare may be utilized. The present invention may be practiced by utilizing any of a variety of known surgical instruments.

The snare loop of the present invention has been disclosed as being an electrically conductive snare loop, such as a monopolar cutting wire. However, it is not required that an electrically conductive snare loop be utilized in the present invention. For example, a snare loop could be utilized that would cut the polyp from the body by constricting the snare loop around the polyp and using the physical constriction of the snare loop to cut the polyp. Accordingly, if the snare loop is not electrically conductive, the snare could be attached to the injection needle through any attachment means and the attachment means would not be required to be electrically conductive. Therefore, an electrically conductive snare loop is not required in the present invention.

The disclosed embodiments are illustrative of the various ways in which the present invention may be practiced. Other embodiments can be implemented by those skilled in the art without departing from the spirit and scope of the present invention.

What is claimed is:

1. A surgical instrument assembly comprising:
    a body;
    an actuator, said actuator slidably attached to said body for sliding movement on said body;
    a catheter, said catheter attached to and extending through said body at a proximal end of said catheter;
    an injection needle, said needle disposed within said catheter and having a proximal end connected to said actuator and a distal end containing a piercing tip, said needle movable within said catheter between a first position wherein said distal end of said needle extends beyond a distal end of said catheter and a second position wherein the distal end of said needle is retracted within said catheter; and
    a snare, said snare attached to the distal end of said injection needle.

2. The surgical instrument assembly of claim 1 further comprising:
    a first lumen, said first lumen contained within said catheter and wherein said injection needle is disposed within said first lumen;
    a second lumen, said second lumen contained within said catheter,
    a retrieval device, wherein said retrieval device is contained within said second lumen; and
    a second actuator, said second actuator disposed on said body for sliding movement on said body and wherein said retrieval device is connected to said second actuator at a proximal end of said retrieval device and wherein said retrieval device is movable within said second lumen between a first position wherein said retrieval device extends beyond a distal end of said catheter and a second position wherein said retrieval device is retracted within said catheter.

3. The surgical instrument assembly of claim 2 wherein said retrieval device is a forceps apparatus.

4. The surgical instrument assembly of claim 2 wherein said retrieval device is a net.

5. The surgical instrument assembly of claim 1 wherein said snare is attached to said injection needle by a weld joint.

6. The surgical instrument assembly of claim 1 wherein said snare is bent at a location along said snare that is distal to the attachment point between said needle and said snare.

7. The surgical instrument assembly of claim 1 wherein said snare is a monopolar cutting wire.

8. The surgical instrument assembly of claim 1 wherein said needle includes a first electrically conducting portion and a second non-electrically conducting portion, wherein said first portion is joined to said second portion by an electrically conducting coupler and wherein said snare is attached to said electrically conducting coupler.

9. A surgical instrument assembly for use in tissue removal procedures, comprising:
   an endoscope assembly, said endoscope assembly including a working channel;
   an injection needle, said injection needle including a distal end containing a piercing tip and a proximal end;
   a snare, said snare attached to the distal end of said injection needle; and
   an actuator, said actuator connected to said injection needle at the proximal end of said needle for movement of said needle between a first position where the distal end of said needle extends beyond a distal end of said working channel and a second position where the distal end of said needle is retracted to a position proximal of said distal end of said working channel.

10. The surgical instrument assembly of claim 9 further comprising:
   a first lumen, said first lumen contained within said working channel and wherein said injection needle is disposed within said first lumen;
   a second lumen, said second lumen contained within said working channel;
   a retrieval device, wherein said retrieval device is contained within said second lumen; and
   a second actuator, said second actuator connected to said retrieval device at the proximal end of said retrieval device for movement of said retrieval device between a first position where the distal end of said retrieval device extends beyond a distal end of said working channel and a second position where the distal end of said retrieval device is retracted within said working channel.

11. The surgical instrument assembly of claim 10 wherein said retrieval device is a forceps apparatus.

12. The surgical instrument assembly of claim 10 wherein said retrieval device is a net.

13. The surgical instrument assembly of claim 9 wherein said snare is a monopolar cutting wire.

14. The surgical instrument assembly of claim 9 wherein said snare is bent at a location along said snare that is distal to the attachment point between said needle and said snare.

15. The surgical instrument assembly of claim 9 further comprising:

a second working channel, said second working channel attached to said endoscope assembly along the length thereof and wherein said injection needle is disposed within said second working channel; and a hood, said hood attached to the distal end of said endoscope assembly.

16. The surgical instrument assembly of claim 15 wherein said hood is made from an optically clear material.

17. The surgical instrument assembly of claim 15 wherein a top of said hood is configured at an angle with respect to a base of said hood.

18. The surgical instrument assembly of claim 17 wherein when said needle is in said first position, said snare is disposed in front of the top of said hood in a coplanar relationship.

19. A method of removing tissue from a body of a patient comprising the steps of:
   inserting a distal end of a catheter into the body of the patient;
   extending an injection needle and a snare through the distal end of the catheter, said snare attached to a distal end of said injection needle;
   injecting a fluid into the tissue to be removed from the body;
   capturing the tissue to be removed by said snare;
   conducting an electrical current through said needle and into said snare; and
   cutting the tissue by said snare.

20. The method of claim 19 further comprising the steps of:
   extending a tissue retrieval device from the distal end of the catheter;
   capturing the cut tissue by said retrieval device; and
   removing the tissue from the body.

21. The method of claim 19 further comprising the step of retracting said injection needle into said catheter after the step of injecting the fluid into the tissue to be removed and prior to the step of capturing the tissue to be removed by said snare.

22. An apparatus for injecting fluid into tissue to be removed from a body and capturing the tissue to be removed, comprising:
   a catheter, said catheter including a distal end for insertion into a body;
   an injection needle, said injection needle disposed within said catheter and including a piercing tip at a distal end thereof; and
   a snare, said snare attached to said injection needle at the distal end thereof;
   wherein said injection needle is movable within said catheter between a first position where the distal end of said needle and said snare extend beyond the distal end of said catheter and a second position where the distal end of said needle and said snare are retracted within said distal end of said catheter.

23. The apparatus of claim 22 wherein said snare is a monopolar cutting wire.

24. The apparatus of claim 22 wherein said snare is bent at a location along said snare that is distal to the attachment point between said needle and said snare.

25. The apparatus of claim 22 wherein said injection needle includes a first rigid structural portion and a second flexible structural portion.

* * * * *